United States Patent [19]
Osterweil

[11] Patent Number: 6,049,281
[45] Date of Patent: Apr. 11, 2000

[54] METHOD AND APPARATUS FOR MONITORING MOVEMENTS OF AN INDIVIDUAL

[76] Inventor: Josef Osterweil, 5411 Amberwood La., Rockville, Md. 20853

[21] Appl. No.: 09/162,147

[22] Filed: Sep. 29, 1998

[51] Int. Cl.[7] .................................................. G08B 23/00
[52] U.S. Cl. ................................. 340/573.4; 340/573.1; 340/573.7; 600/473
[58] Field of Search ................................. 340/552, 555, 340/556, 557, 565, 567, 573.1, 573.4, 573.7, 575; 348/154, 155, 169; 600/473, 534

[56] References Cited

U.S. PATENT DOCUMENTS

| | | | |
|---|---|---|---|
| 4,458,266 | 7/1984 | Mahoney | 358/105 |
| 5,107,845 | 4/1992 | Guern et al. | 600/473 |
| 5,253,070 | 10/1993 | Hong | 358/209 |
| 5,339,104 | 8/1994 | Hong | 348/155 |
| 5,396,284 | 3/1995 | Freeman | 348/154 |
| 5,410,297 | 4/1995 | Joseph et al. | 340/573.1 |
| 5,505,199 | 4/1996 | Kim | 600/323 |
| 5,757,287 | 5/1998 | Kitamura et al. | 340/937 |
| 5,844,488 | 12/1998 | Musick | 340/573.4 |
| 5,884,249 | 3/1999 | Namba et al. | 704/9 |

*Primary Examiner*—Daniel J. Wu
*Assistant Examiner*—Van T. Trieu
*Attorney, Agent, or Firm*—Steven Wegman

[57] ABSTRACT

Monitoring an individual to determine when the individual is likely to exit a supportive structure. An apparatus has an image capturing device that captures successive images of the monitored individual in the supportive structure. A processing device compares a current captured image to a previous image to detect predetermined characteristics of the monitored individual with respect to the supportive structure. An alarm is actuated when it is determined that the detected predetermined characteristics exceed predetermined threshold values for at least one of the predetermined characteristics.

58 Claims, 4 Drawing Sheets

METHOD AND APPARATUS FOR MONITORING MOVEMENTS OF AN INDIVIDUAL

1. Field of the Invention

The present invention generally rela0tes to a monitoring device for alerting monitoring personnel when a monitored individual appears to attempt to leave a bed, etc., and may be about to fall. The present invention relates more specifically to a monitoring device for the detection and monitoring of the presence or absence of a person from a bed, chair, or other supportive structure and the patient's movement within the supportive structure, so as to ensure the safety of a patient (individual) occupying such supportive structure.

2. Background Information

A problem well known to medical and senior service providers is that of making sure certain patients, such as, for example, hospital patients, individuals in a convalescence facility or elderly individuals residing in a nursing/assisted living facility, remain in their bed. Reasons for this include, for example, the need to quickly locate the individual, administer medical treatment to the correct individual, and most importantly, to avoid injury to the individual should he/she fall while exiting the supportive structure without assistance. Such knowledge is particularly important when the individual becomes disoriented due to, for example, illness or medication.

Medical bed and chair occupancy monitoring systems have been devised to assist medical providers with monitoring the presence or absence of a person in their supportive structure (e.g., bed). Such systems are typically equipped with an alarm or are electronically tied to a common monitoring location, such as, for example, a nurse's station. Such devices generally employ some type of electro or electro-mechanical switch to sense the individual's exiting from the supportive structure.

For example, Applicant's prior U.S. Pat. No. 4,858,622 discloses a fall alert system utilizing a magnetically operable switch. One end of a harness is secured to the individual being monitored. The remaining end of the harness has a ferromagnetic shunt that is held to a sensor by magnetic attraction. Should the monitored individual fall, the shunt detaches from the sensor, alerting the monitoring personnel.

Such a system suffers from certain inherent problems. For example, if the above described harness is short, the sensitivity of the monitoring device will be increased. However, permissible movement by the monitored individual will be severely restricted if false alarms are to be avoided. On the other hand, if one attempts to minimize such inconvenience to the monitored individual, the length of the harness must be increased. Increasing the length of the harness permits a certain degree of movement by the individual without activating the monitoring device, but reduces the sensitivity of the monitoring device. As a result, such systems may only alert monitoring personnel that an individual, such as a hospital patient, has already exited (and/or possibly fallen out of) the supportive structure. That is, such systems do not issue an alert to the monitoring individual indicating that the monitored individual is about to exit the supportive structure.

In addition, in most existing fall alert systems, in the situation in which a person is bed-ridden, a caretaker will regularly attend to the person to, for example, change the bedding and attend to the person's personal hygiene. In such situations, the person is moved about, resulting in the undesired triggering of the monitoring device.

It is therefore an object of the present invention to provide a new (e.g., novel) approach to monitoring individuals that permits the unrestricted movement of the individual in a supportive structure without compromising its reliability. A further object of the present invention is to provide such a device with a mechanism for temporarily disabling the device while an authorized caretaker is attending to the monitored individual.

It is a further object of the present invention to provide an optical system that replaces the existing electro or electro-mechanical triggering switches for monitoring the presence of a patient. It is another object of the present invention to provide a monitoring device that may be used as a portable unit or may be built into a monitoring location to monitor a bed, chair or similar supportive structure to sense the presence or absence of a person normally occupying the structure.

SUMMARY OF THE INVENTION

According to the present invention, a new approach for optically monitoring an individual is disclosed comprising a monitoring system that includes a manual and/or automatic disabling feature. The optical monitoring device employs at least one optical sensor on which an image corresponding to the supportive structure, as well as the periphery, is formed. The number of elements in the array determines the resolution of the monitoring system. However, since the present invention is primarily concerned only with the detection of movement in a monitored area, and not with specific features of the monitored individual, a high resolution ("fine image") is not necessary for the implementation of the present invention. A low resolution ("coarse image") is sufficient for determining movement in the supportive structure.

The image captured by the optical sensor represents a light depiction of the supportive structure (e.g., bed) area. Successive images are captured by the optical sensor over time. The optical sensor outputs a signal representing the captured image, which is then processed to determine the monitored individual's relative position to the bed as a function of time. The dynamics of the monitored individual's motion is analyzed to determine the probability that a patient (individual) is about to leave the supportive structure (such as, for example, a bed) and/or a fall is imminent. That is, the patient's location and movement is analyzed to determine the body's position, velocity and/or acceleration towards a predetermined boundary indicating that a supportive structure (bed) exit may occur.

When the monitoring device determines that a bed exit, and perhaps a fall, may be imminent, an alarm is activated to alert monitoring personnel, at, for example, a local or remote monitoring site. The alarm may be visual (e.g., a light) or audible (e.g., an acoustic annunciator). According to an embodiment of the present invention, a visual image of the area being monitored is provided to the monitoring personnel, so as to provide a visual confirmation that a bed exit is imminent (or has occurred). Alternatively, another embodiment is provided in which a two-way audio communication is performed between the monitored individual and the monitoring personnel to confirm that the monitored individual has exited the supportive structure.

The monitoring device is provided with an alarm disable feature, so that attending personnel, such as, for example, a caretaker or family member, can provide services to the monitored individual without activating the alarm. When the caretaker is finished rendering assistance to the individual being monitored, the monitoring device is re-activated.

According to an embodiment of the present invention, a switch is actuated by the caretaker to deactivate the monitoring device. When the caretaker has completed rendering assistance to the monitored individual, the caretaker manually re-activates the device. Alternatively, the monitoring device may automatically re-arm (re-activate) itself a predetermined period of time after the caretaker deactivates the device. In this situation, an indicator, which may be visual or audible, at the bed (supportive structure) site and/or a monitoring station (e.g., caretaker's station), may be provided to alert the caretaker that the monitoring device will shortly be fully operational. In this way, the caretaker can re-actuate the switch, thus resetting the time period, if additional assistance time is required.

According to another embodiment of the present invention, a passive deactivation system is employed. For example, a specially encoded card, IR transmitter, RF transmitter or transponder, or other identification device can be, for example, carried in the pocket of the caretaker or worn around the caretaker's neck. A receiver associated with the monitoring device recognizes the card or transmitter as belonging to a caretaker, and thus deactivates the monitoring device. According to a variation of the present invention, the cards and/or transmitters are uniquely coded. The monitoring device records certain information, such as, for example, the date, the code that deactivated the monitoring device, and the time the device was deactivated and reactivated, so as to provide a log showing all the authorized individuals that assisted the monitored individual.

An apparatus is disclosed for determining when a monitored individual is likely to exit a supportive structure, comprising:

an image capturing device that captures successive images of the monitored individual in the supportive structure;

a processing device that processes the captured image to detect predetermined characteristics of the monitored individual with respect to the supportive structure, by comparing the captured image to a previous image; and an alarm that is actuated when the processing device determines that the detected predetermined characteristics exceed predetermined threshold values for at least one of the predetermined characteristics.

According to an advantage of the present invention, the image capturing device detects at least one of visible light and infrared light emitted by the monitored individual and supportive structure.

According to an advantage of the present invention, an image signature database is provided that stores each image captured by the image capturing device. A plurality of stored images are provided to the processing device, for analysis along with said captured image, to detect the predetermined characteristics.

According to another advantage, the alarm is provided to a monitoring site remote from the monitored individual. Further, an alarm inhibitor is provided that enables a caretaker to render assistance to the monitored individual without actuating the alarm. The alarm inhibitor can be enabled by a manual actuation of a switch. The actuation of the switch causes a timer to start counting. The alarm is prevented from being actuated until such time as the counter reaches a predetermined period of time.

Instead of a manually operated switch, a passive system, comprising a transmitter and a receiver, may be used. A caretaker has the transmitter (transponder) in his/her possession. A receiver, associated with the monitoring device, prevents actuation of the alarm as long as the receiver receives the signal transmitted from the transmitter. Alternatively, the image capture device detects the presence of the caretaker based upon a direction of movement of a second moving object (e.g., a second moving person) detected by said image capturing device. When the image processor detects that the movement of the second moving person is towards a center of the bed, the alarm is prevented from being actuated.

According to an object of the present invention, an apparatus determines when a monitored individual is likely to exit a supportive structure. The apparatus comprises means for capturing successive images of the monitored individual in the supportive structure, means for processing the captured images to detect predetermined characteristics of the monitored individual with respect to the supportive structure, by comparing a current captured image to a previous captured image, and means for indicating that the monitored individual is likely to exit the supportive structure when the processing means determines that the detected predetermined characteristics exceed predetermined threshold values for at least one of the predetermined characteristics.

According to an advantage of the invention, the capturing means comprises a sensor that detects visible light emitted by the monitored individual and the supportive structure. Alternatively, the sensor detects visible and infrared light emitted by the monitored individual and the supportive structure.

A feature of the present invention resides in means for inhibiting the indicating means when a caretaker renders assistance to the monitored individual. The inhibiting means may be, for example, a switch (such as, for example, a pressure sensitive floor mat switch or floor deflection detecting switch), and may also include, for example, a delay device that prevents the indicating means from indicating that the monitored individual is likely to exit the supportive structure for a predetermined period of time upon an actuation of the switch. Alternatively, the inhibiting means may comprise a transmitter that is in the possession of the caretaker, and a receiver that receives a signal transmitted by said transmitter, or a voice recognizing device.

According to the disclosed embodiments, the indicating means is prevented from indicating that the monitored individual is likely to exit the supportive structure as long as the receiver receives the signal transmitted by the transmitter. The indicating means may be prevented from indicating that the monitored individual is likely to exit the supportive structure as long as the processing means detects that a second moving object proximate the monitored individual is moving towards a center of the supportive structure.

According to a feature of the instant invention, the processing means determines at least one of a relative position, a velocity, and an acceleration of the monitored individual relative to the supportive structure.

According to a feature of the instant invention, the indicating means may be either an audible alarm and/or a visual alarm. In addition, the present invention may include means for remotely alerting an individual distant from the monitored individual that the monitored individual is likely to exit the supportive structure.

According to an object of the present invention, a method is disclosed for determining when a monitored individual is likely to exit a supportive structure, by capturing successive images of the monitored individual (using, for example, an image capturing device) in the supportive structure, processing the captured images to detect predetermined characteristics of the monitored individual with respect to the supportive structure, by comparing a current captured image to a previous image, and indicating that the monitored individual is likely to exit the supportive structure when it is determined that at least one predetermined characteristic exceeds a predetermined threshold value.

According to an advantage of the present invention, the processing of captured images comprises analyzing the captured images to determine at least one of a relative position, a velocity, and an acceleration of the monitored individual relative to the supportive structure.

According to another advantage of the present invention, the indicating that the monitored individual is likely to exit the supportive structure comprises alerting an individual remote from the monitored individual.

Another object of the present invention resides in an apparatus that determines when a monitored individual is likely to exit a supportive structure. This is accomplished by having an image capturing device that captures successive images of the monitored individual in the supportive structure, an image processing device that processes the captured images to detect at least one of a relative position, a velocity and an acceleration of the monitored individual with respect to the supportive structure, by comparing a current captured image to a previous image, a motion threshold setting device that sets a predetermined characteristic for at least one of the relative position, velocity and acceleration of the monitored individual with respect to the supportive structure, an alarm that is actuated when at least one of the detected relative position, velocity and acceleration exceeds the predetermined characteristic, and an alarm inhibitor that inhibits the alarm when a caretaker renders assistance to the monitored individual.

According to a feature of the present invention, the alarm is actuated at a monitoring station. However, a monitoring station communicator may be provided that transmits at least one of image, status and control signals to a mobile alert device. In addition, a display unit may be located at the monitoring station to provide a visual indication of the monitored individual.

According to an advantage of the instant invention, an image signature database is provided that stores each image captured by the image capturing device. A plurality of stored images are provided to the image processing device, along with a current captured image, in order to detect at least one of the relative position, velocity and acceleration.

Another advantage of the present invention resides in the inclusion of an information inserting device that provides predetermined data related to the monitored individual. The predetermined data may comprise, for example, at least one of a name of the monitored individual and a location of the monitored individual. In addition, either a sequencing device (that sequentially displays images of a plurality of monitored individuals on the display unit), or a screen splitting device (that enables images of a plurality of monitored individuals to be simultaneously displayed on the display unit) may be provided.

BRIEF DESCRIPTION OF THE DRAWINGS

The foregoing and other objects, features and advantages of the invention will be apparent from the following more particular description of preferred embodiments of the invention, as illustrated in the accompanying drawings in which reference characters refer to the same parts throughout the different views. The drawings are not necessarily to scale, emphasis instead being placed upon illustrating principals of the invention in a clear manner.

DETAILED DESCRIPTION OF THE PREFERRED EMBODIMENTS

In the following discussion, the present invention will be described installed in a nursing home environment to monitor a patient in a bed. However, it is understood that the present invention is applicable in other environments, such as, but not limited to, a hospital, an assisted living environment, or a home of an elderly or infirm individual. Furthermore, while the present discussion will center around monitoring an individual lying in a bed, it is understood that the present invention is applicable to any device that supports an individual, such as, but not limited to, a chair, a wheelchair, a traction recovery device, or other supportive structure.

Figure 1:
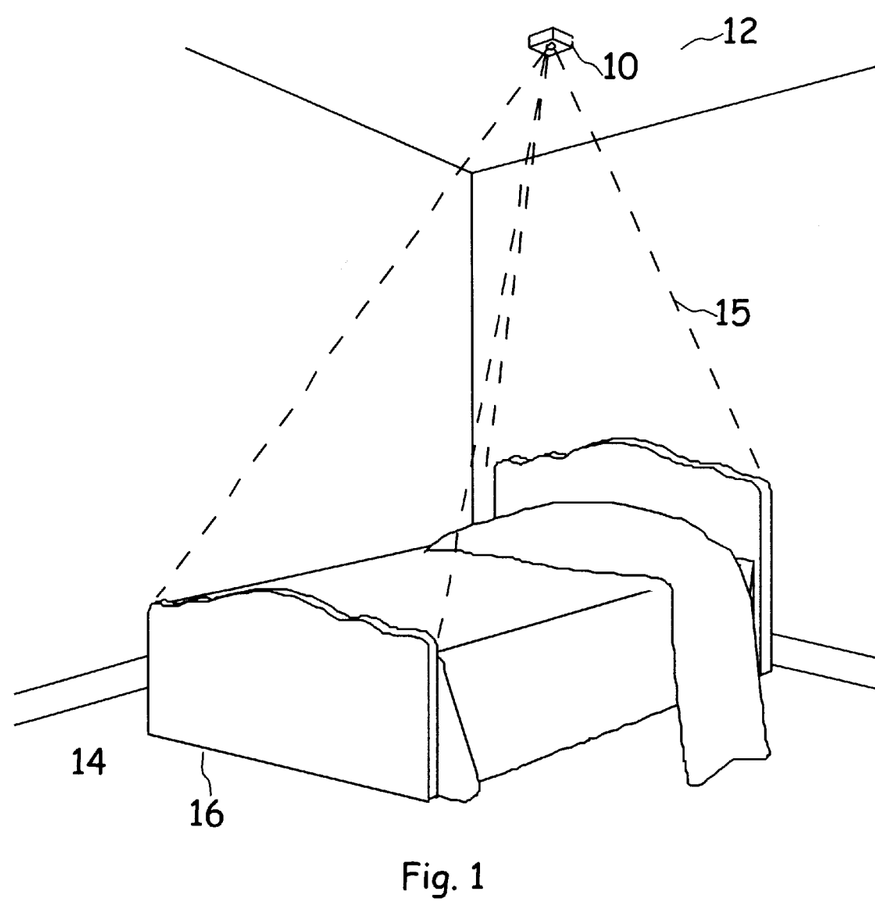
FIG. 1 illustrates a placement of a monitoring device to cover an area that includes a support structure, such as, for example, a hospital bed.

FIG. 1 illustrates a monitoring device 10 of the present invention mounted to a ceiling 12 of a nursing home room 14. However, it is understood that the monitoring device 10 may be mounted to other than the ceiling 12. For example, the monitoring device 10 may be attached to a tripod (not shown) placed on the ground, or to a wall. The preferred embodiment mounts the monitoring device 10 on the ceiling of the nursing home room 14 above the center of a bed 16, ensuring full coverage of a single bed. The specific manner in which the monitoring device is mounted is not critical; what is important, is that the monitoring device is positioned so that a fan-shaped detecting zone 15 of the monitoring device 10 "covers" the bed 16. In addition, while the present invention will be described with respect to a single bed, it is understood that the monitoring device 10 can watch ("cover") individuals in multiple beds, by increasing the fan-shaped detecting zone 15 (through the use of wide angle optics) to "cover" plural beds. Such optics are known to those skilled in the art, and thus, are not discussed herein.

In the illustrated embodiment, the monitoring device is housed inside a protective enclosure (not numbered) that is mounted to the ceiling 12. However, the present invention could dispense with the enclosure, if, for example, the monitoring device is "built into" the ceiling 12, without diverting from the scope and/or spirit of the present invention.

Figure 2:
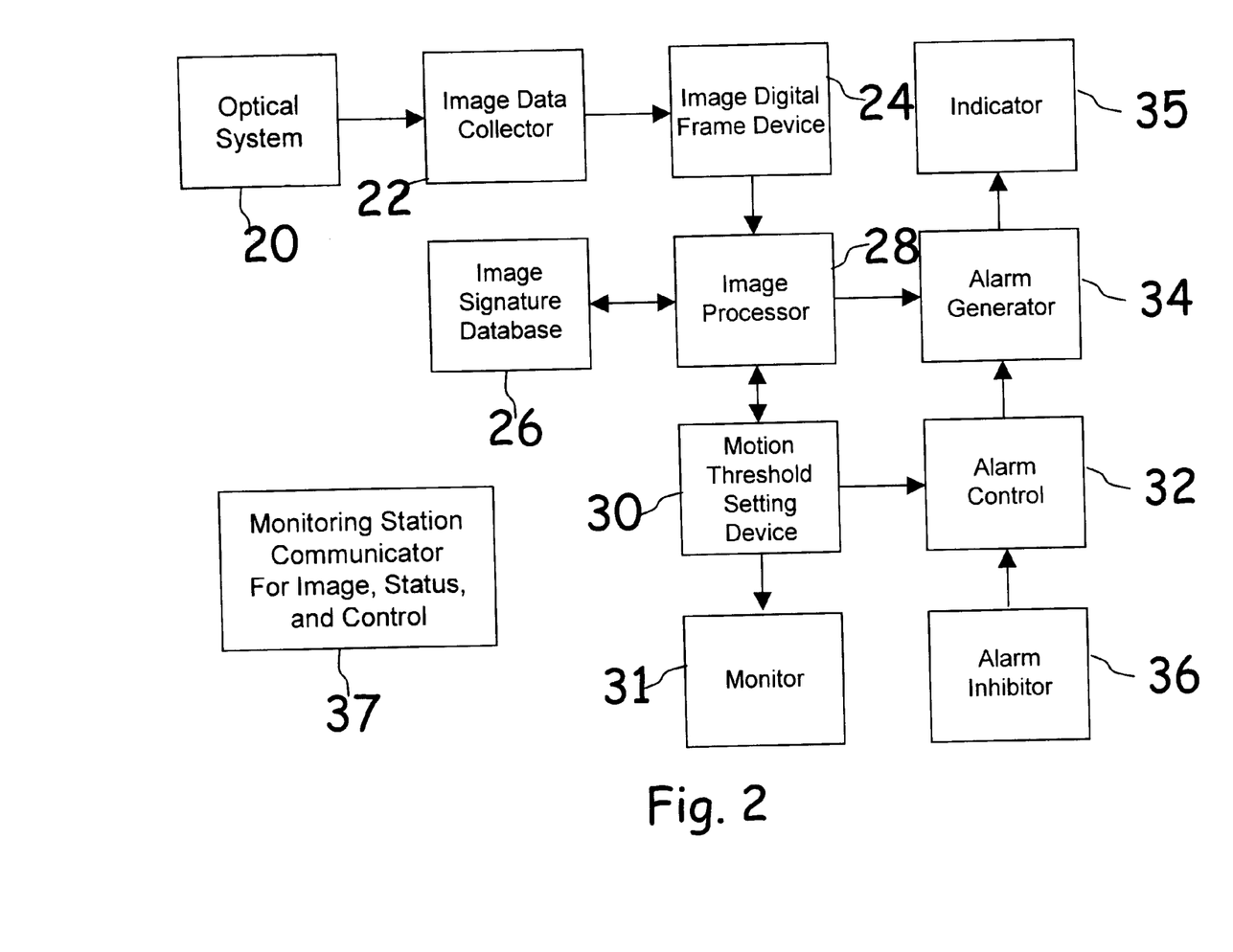
FIG. 2 illustrates a block diagram of the monitoring device illustrated in FIG. 1.

As shown in FIG. 2, the monitoring device 10 comprises an optical system 20, an image data collector 22, an image digital frame device 24, an image signature database 26, an image processor 28, motion threshold parameter setting device 30, a monitor 31, an alarm controller 32, an alarm generator 34, an alarm indicator 35, and an alarm inhibitor 36.

In the disclosed embodiment, the optical system 20 and imaging sensing element 22 are located at the location of the person to be monitored, while the remaining elements of the monitoring device are remotely located. The imaging sensing element (camera) 22 is electrically interfaced to the remaining elements. The electrical interface may comprise, for example, a fiber optic cable, a video cable (such as, for example, RG-6 cable), a twisted pair wire (such as, for example, category 5 wire), or a wireless transmission link. However, it is understood that all the elements comprising the present invention, absent the monitor 31 and associated alarm, may be located at the location of the person being monitored.

The signal provided by the camera 22 may be an analog signal or a digital signal. Further, the signal may be compressed if desired. It is noted that the transmission speed of the video signal is dependent upon the capability of the transport medium used to carry the signal. For example, a fiber optic cable has a wide bandwidth, and thus can transmit a video signal at a high speed without the need to compress the signal. On the other hand, a twisted pair cable, such as is used to transmit telephone signals or with a hospital/nursing home call system, is a low bandwidth medium, and thus, requires that a video signal be transmitted at a low data rate. In this case, the effective transmission rate of such a medium may be improved by compressing the video signal.

In addition, when a low bandwidth transmission medium, such as, for example, twisted pair wiring is employed, it is desirable to decrease the refresh rate of the image being transmitted. That is, when a fast transmission link (e.g., video cable or fiber optic cable) is employed, the instant invention may be configured to operate with a high refresh rate (e.g., 30 or more frames per second). However, when the low bandwidth transmission medium (e.g., twisted pair wire) is used, the instant invention is configured to operate with a low refresh rate (e.g., less than 30 frames per second).

The optical system 20 comprises an optical element that captures and focuses an image of the hospital bed and its surrounding periphery. The optical sensor 20 focuses light, corresponding to the image, onto a focal plane of the optical sensor, and scans the image into the sensor (if the optical sensor is other than a two-dimensional sensor). In addition, the optical sensor can optionally filter the light that impinges the sensor, so as to provide for one (or more than one) spectrum sensing capabilities. In the preferred embodiment, a camera, such as, for example, a charge coupled device (CCD) image detector is employed. However, other types of analog or digital sensors, such as, but not limited to, for example, linear scanning and/or multi-dimensional (e.g., two or more) line sensors that cover the infrared (IR) and/or visible light spectrum, and/or other predetermined wavelength (light spectrum) range, or a wide spectral image charge-injection device (CID) camera, such as manufactured by, for example, Cidtec in Liverpool, N.Y., may be employed without diverting from the spirit and/or scope of the invention.

The sensitivity of the employed camera determines whether additional (external) illumination of the monitored area is required. Further, the use of a combination of IR and visible light images simplifies the distinguishing between the individual, the bed 16 and inanimate objects on the bed. However, the present invention can be implemented using only IR light or visible light without departing from the spirit and/or scope of the instant invention.

The image captured by the camera 20 represents an IR and/or visible light depiction of the bed area. Successive image captures constitute a series of individual and bed depiction records over time. The images are processed (to be described below) to determine the monitored individual's relative position to the bed over time. The dynamics of the individual's position and motion provides a clue as to the probability that a bed exit (and/or fall) is imminent.

As indicated above, the camera 20 is positioned so that the fan-shaped detection zone 15 covers the top of the bed 16. If a camera with a large sensor array is employed, the precision with which the camera is aimed at the bed is not critical. In such circumstances, a large sensor array obtains information with sufficiently high resolution to be able to derive the bed outline by subsequent image processing. A single sensor camera (or a camera utilizing a small array) requires more accurate optical alignment to detect the edges of the bed.

It should be noted that alignment aids (not shown) may be utilized to assist in the optical alignment of the camera. Such alignment aids may include, for example, a visible light beam that is emitted from the monitoring device 10 to indicate the coverage area of the fan-shaped detection zone 15, thus facilitating the aiming of the monitoring device 10 at the corners of the bed 16, and is similar to, for example, alignment aids employed with x-ray cameras (scanning devices). While such alignment aids facilitate the set-up of the present invention, it is understood that the presence or absence of such alignment aids are not essential to the proper installation (set-up) of the present invention.

The images captured by the camera 20 impinge upon the image data collector 22. The image data collector (image data collection focal plane) 22 comprises one or more image sensing elements. As noted above, the image sensing element may be a multi-dimensional sensor, such as, for example, commonly employed in cameras, a linear sensor which requires an external scanning in one direction, or a single pixel sensor which requires scanning in at least two directions.

The output of the image data collector 22 is provided to an image digital frame device 24, which converts the signals generated by the image data collector 22 into digital image frames. According to the present invention, quantization of the analog-to-digital conversion can be selected based upon the granularity required for the image processing.

The output of the image digital collector 24 is inputted to an image processor 28. The image processor 28 employs image processing techniques to identify the patient (monitored individual) and his relative position and/or velocity and/or acceleration related to the environment, in general, and to the bed, in particular. It is understood that the present invention is not limited to the use of any specific image processing techniques. Current processing techniques, along with image processing techniques to be developed, may be employed without diverting from the spirit and/or scope of the instant invention. For example, algorithms (processes) for pattern recognition techniques, edge detection, neural networks, temporal analysis of successive images, or fuzzy logic techniques may be employed. Furthermore, combinations of these processes can be utilized to provide an outline of the patient's body (or part thereof) as well as its position changes as a function of time. Such algorithms and processes are well known to those skilled in the art of pattern recognition/detection, and thus, are not discussed in detail herein.

Further, the sophistication of the image processing and algorithm(s) may vary, based upon the hardware employed. Accordingly, as new and/or improved sensors are developed, modifications to the image processing may be required. However, the present invention is not limited to the use of a specific sensor and/or image process, and thus, a specific processing algorithm, but to the concept of capturing an image of a monitored individual to determine whether the monitored individual is about to exit a support structure.

In order to enhance the differentiation of the patient and the bed, the optical system 20 can be configured to employ both infrared and visible light. The detection of infrared energy corresponds to heat given off from an object. Objects such as, for example, chairs and beds give off very little, if any, infrared energy. On the other hand, a human body produces larger quantities of infrared heat. The use of two light bands (e.g., visible light and infrared light) improves the ability of the system to identify a person from among a plurality of objects in a captured image.

In the present invention, an image signature database 26, that is bi-directionally interfaced to the image processor 28, is provided to enhance the detection process. Historical data on the "scanned" area (e.g., images of past image captures) is stored in the image signature database 26. This data is used by the image processor 28 to improve the detection accuracy of the present invention, based upon an adaptive detection process, in which multiple past captured images are compared to a present captured image to detect differences in the images corresponding to movement of the monitored individual.

While the embodiment of the present invention discloses the use of the image signature database 26, circuit simplification (and thus, cost reductions) can be achieved by the omission of the image signature database 26. Accordingly, it is understood that while the image signature database 26 functions to enhance the detection operation, the image signature database 26 can be deleted without departing from the spirit and/or scope of the present invention.

The preferred embodiment of the instant invention includes a motion threshold parameter setting device 30 in which the image data is evaluated (compared) against predetermined threshold parameters, such as, for example, position, and/or velocity, and/or acceleration set points. When at least one predetermined threshold parameter setting is exceeded, an alarm is actuated. In the disclosed embodiment of the invention, monitoring personnel can vary the predetermined threshold parameter settings. In addition, provisions are provided to enable the monitoring personnel to manually enhance the bed (supportive structure) outline on an associated monitor 31. For example, in the preferred embodiment, a cursor (e.g., a digitizing pad with a puck, a mouse, etc.) is provided that enables the monitoring personnel to, for example, select a particular bed to view from among a plurality of beds, in the situation in which plural beds are being monitored, to enlarge the view of the selected bed to allow the monitoring personnel to better view the actions of the monitored individual, or to vary the predetermined threshold parameter settings.

Figure 8:
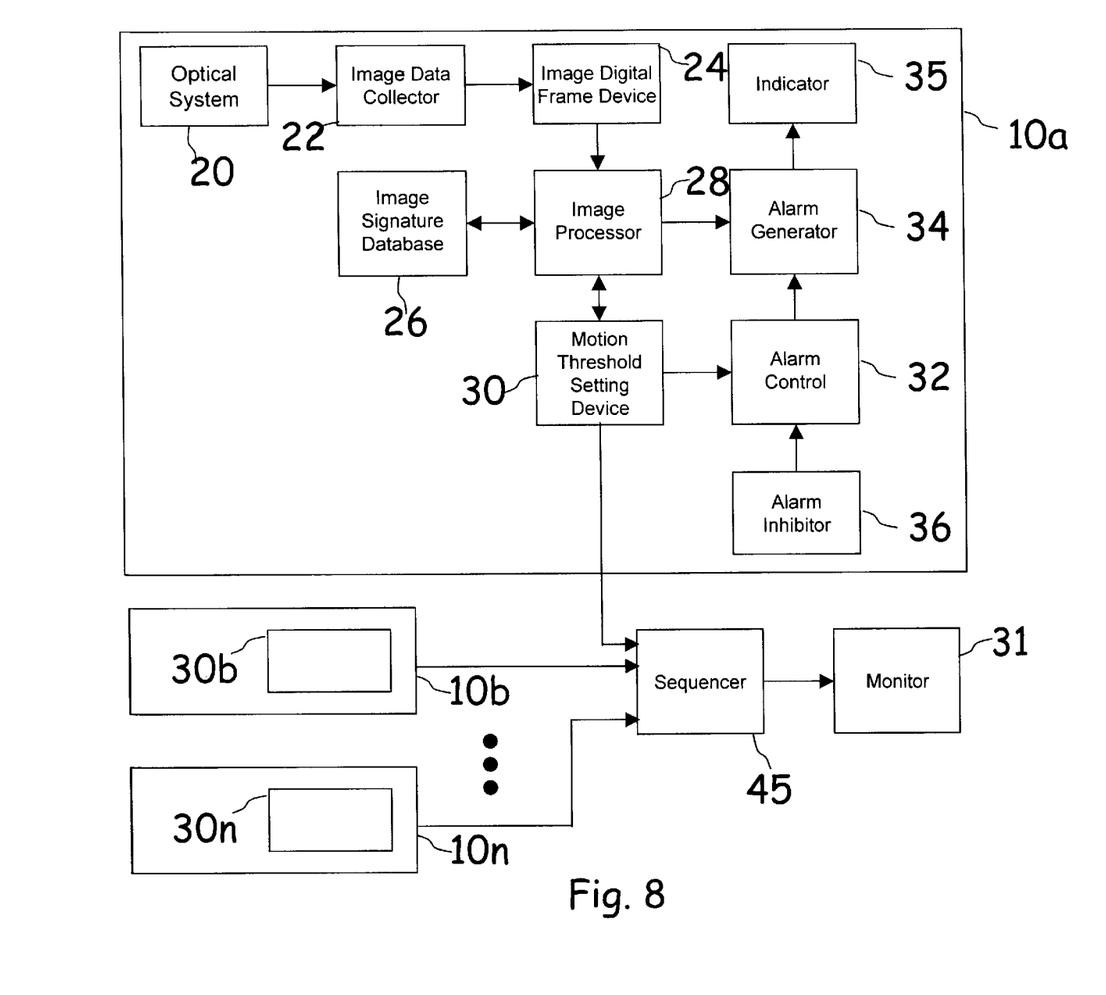
FIG. 8 illustrates a variation of the instant invention, in which a sequencer/splitter device is provided to enable the display of multiple monitored individuals on a monitor.

In the disclosed invention, one monitor is used to monitor one individual. As a result, a monitor 31 must be provided for each individual to be monitored. In order to reduce the number of monitors that are needed to observe plural monitored individuals, FIG. 8 discloses a variation of the invention, in which plural monitoring devices 10a–10n are connected to a sequencer/splitter device 45. The elements comprising monitoring devices 10a–10n correspond to like numbered elements in FIG. 2, and hence, need not be described again. As shown in FIG. 8, the sequencer/splitter device 45 accepts the output from plural motion threshold setting devices 30a–30n associated with respective imaging devices 10a–10n, in order to enable the monitoring of plural individuals on the monitor 31.

A video sequencer, manufactured, for example, by GBC or Remington, and commonly employed in the surveillance field, may be used to enable a plurality of monitored individuals to be watched on a single monitor. In such a situation, the sequencer cycles the plurality of video signals to the single monitor every 4 seconds, for example. Further, an over-ride mechanism can be provided so that when an alarm occurs (indicating that a particular person is about to exit the bed), that signal is given priority and displayed on the monitor. Still further, a high risk individual (e.g., a monitored individual that frequently attempts to exit their bed) may be sequenced at a higher rate than a non-high risk individual. That is, if, for example, there are four individuals (1 high risk individual and 3 non-high risk individuals) that are being sequentially monitored on the one monitor, the system can be configured to display, for example, the high risk individual, the first non-risk individual, the high risk individual, the second non-high risk individual, the high risk individual, and then the third non-high risk individual.

Alternatively, a screen splitter, such as, for example, quad screen splitter model 42155 manufactured by ATV, Inc., may be used to simultaneously display a plurality of small (e.g., 4, using the ATV splitter) images (windows) on the single monitor. Further, an over-ride mechanism can be provided so that a single, fill screen image is shown when an alarm occurs.

Further, it is possible to combine the screen splitter with the video sequencer, so that even more individuals can be monitored on a single monitor. In such a situation, it is desirable to constantly display the high risk patient(s) in one (or more) window, while the remaining windows sequence between different (non-high risk) individuals.

It is desirable to superimpose predetermined information (such as, for example, the monitored person's name, room number, etc.) with the associated image on the monitor. This reduces the time required by the monitoring personnel to identify which individual exited/fell from their bed. However, this feature is not essential to the operation of the present invention.

It is noted that variations of the above may be implemented without departing from the scope and/or spirit of the present invention.

Alternatively, a two-way radio (hardwired or wireless) communication network can be provided between the monitoring location and the plurality of patients being monitored. Such a wireless communication network is referred to as a wireless local area network (WLAN). The WLAN of choice is manufactured by Proxim or Symbol. Both manufacturers employ a standard protocol. However, it is understood that a WLAN from another manufacturer may be used without departing from the scope and/or spirit of the present invention. When the alarm is actuated, a communications link is established (either manually or automatically) between the location at which the individual, which actuated the alarm condition, is and the monitoring site, so that a verbal communication can take place to confirm that the monitored individual actually requires assistance.

While the preferred embodiment discloses the use of the motion threshold setting device 30 to increase the versatility of the monitoring device 10, the monitoring device can be simplified by eliminating the motion threshold setting device 30 and using fixed threshold values. Further, portions of the motion threshold setting device 30 can be omitted without diverting from the scope and/or spirit of the instant invention. For instance, one can eliminate the cursor, or the ability to vary the predetermined threshold parameter settings, without adversely affecting the operation of the present invention or departing from the scope and or spirit of the present invention.

The alarm controller 32 controls the alarm generator 34 to activate an alarm 35 when the monitoring device 10 determines that the dynamics of the individual's position and/or motion indicates that the individual is about to exit the supportive structure (e.g., when the monitored conditions exceed the alert threshold level set by the motion threshold setting device 30) and the alarm inhibitor 36 (to be described below) does not instruct the alarm controller to inhibit an alarm generation.

The alarm generator 34 provides an indication to the monitoring personnel that the monitoring device 10 has determined that the monitored individual is about to exit the supportive structure (e.g., bed). The indication can be, for example, audible or visual. For example, a visual indication can be provided by a flashing lamp on a monitoring panel, or, by an indication on the associated monitor. Alternatively, the visual indication may be implemented by causing the entire monitor screen (or a portion/segment of the monitor display) to flash/blink ON and OFF. An audible alarm can be provided by, for example, a siren or annunciator (e.g., an electronic voice annunciator). The type of alarm provided is not critical to the operation of the present invention.

The alarm generator can be interfaced to an existing call system, if such is provided in a nursing home or related facility (such as, for example, a hospital), or the alarm generator may use a dedicated link. For example, the monitoring device of the present invention may be interfaced to a call system in the manner disclosed in U.S. Pat. No. 4,858,622, the contents of which are expressly incorporated herein by reference in its entirety. Alternatively, the alarm generator 34 can be interfaced to a device that enables the alarm condition to be transmitted over, for example, a telephone line, a network (e.g., wide area network, local area network, Intranet, Internet, etc.) or other wired (or wireless) communications link in which subscriber based transmissions take place using an orderly protocol. The specific manner in which the monitoring device 10 is connected to the location of the monitoring personnel is not critical to the operation of the present system; what is important is that the monitoring personnel are alerted to the exit/fall condition, so that assistance can be rendered to the monitored individual.

The alarm inhibitor 36 comprises a disable function that permits attending personnel, such as a caretaker, to render assistance to the monitored individual without needlessly activating the alarm.

Figure 3:
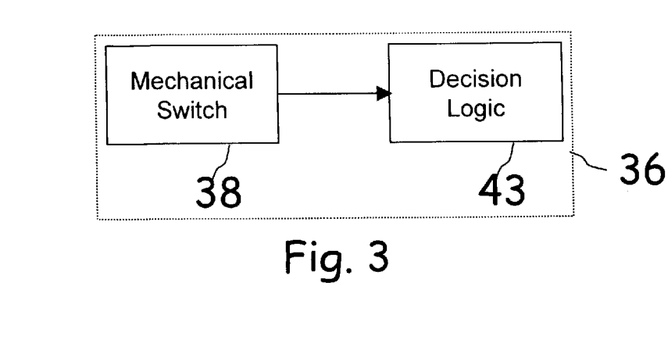
FIG. 3 illustrates a block diagram of an alarm inhibitor used with the monitoring device of the instant invention.

In the disclosed embodiment, the alarm inhibitor 36 (see FIG. 3) includes a switch 38 that is actuated by the attending personnel to inhibit the alarm generation. Switch 38 may comprise, for example, a wall mounted switch, or a pressure sensitive floor mat in which a switch (associated with the floor mat) is actuated when the caretaker steps on the floor mat, or a sensor (of the type employed in the security monitoring field) attached to the floor to detect a deflection in the floor when the caretaker walks on a predetermined location of the floor. When the switch is actuated, a decision logic device 43 of the alarm inhibitor 36 instructs the alarm controller 32 to output an alarm inhibit signal to the alarm generator. Thus, an alarm will not be produced when the caretaker renders assistance to the monitored individual and moves the monitored individual beyond the parameters set by the monitoring device 10.

In the disclosed embodiment, the switch comprises a push button switch. However, the specific type of switch that is used is not critical; a lever switch, a touch sensitive switch, a key operated switch, a keypad type switch, an infrared (IR) controlled switch, or other type of switch may be utilized without departing from the spirit and/or scope of the present invention.

Figure 4:
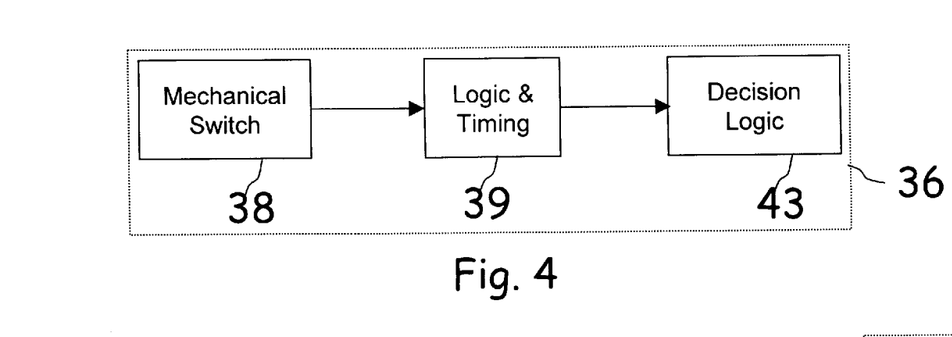
FIG. 4 illustrates a second embodiment of the alarm inhibitor used with the monitoring device of the present invention.

While such a system is simple to produce and very cost-effective, the disadvantage of providing a switch to inhibit the alarm generation is that the caretaker may forget to re-set the switch after the assistance is rendered. In such a situation, the monitored individual could exit/fall out of bed without the monitoring personnel being alerted. Accordingly, in another embodiment (see FIG. 4), the actuation of the switch 38 functions to deactivate the alarm for a predetermined period of time. That is, actuation of the switch 38 starts a timer 39 (which may be either digital or analog) that counts down from a preset time period to zero. Alternatively, the timer 39 can count up from zero to the preset time period. After the expiration of the preset time period, the alarm inhibition is automatically deactivated. In this embodiment, the switch may comprise, for example, a momentary contact type switch.

In a variation of this embodiment, an indication that the preset time period is about to expire is verbally and/or audibly provided to the caretaker. In this variation, the caretaker can re-actuate the switch in order to re-set the timer, thus extending the amount of time that the caretaker can spend with the monitored individual. In this variation, the number of times that the timer can be re-set is not limited.

Another embodiment of the invention employs a transmitter that is either worn or carried by the caretaker. A receiver 40 (see FIG. 5), located proximate the monitored individual, receives a signal transmitted by the transmitter. The receiver 40 and transmitter may operate using, for example, an infrared or radio frequency transmission scheme. The transmission scheme may be analog or digital. For example, a digital spread spectrum radio transmission scheme operating at approximately 900 MHZ may be employed. However, a specific transmission scheme and type is not critical to the operation of the disclosed embodiment, and variations may be made without departing from the spirit and/or scope of the invention.

Figure 5:
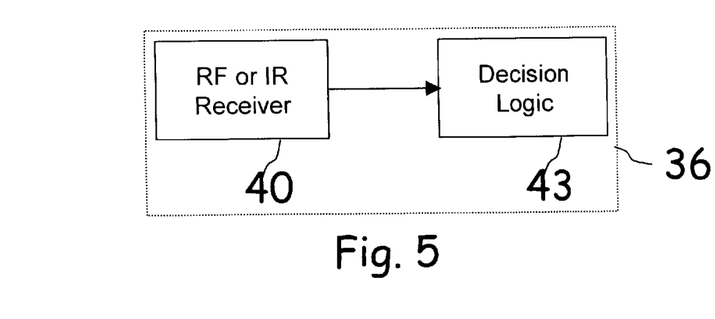
FIG. 5 illustrates a third embodiment of the alarm inhibitor.

As long as the receiver 40 receives the signal from the transmitter, the decision logic device 43 of the alarm inhibitor 36 instructs the alarm controller 32 to output an alarm inhibit signal to the alarm generator 34. Thus, an alarm will not be produced when the caretaker renders assistance to the monitored individual, moving the monitored individual beyond the parameters set by the monitoring device 10. When the caretaker leaves the vicinity of the monitored individual, the receiver 40 loses contact with the transmitter worn or carried by the caretaker. When this occurs, the decision logic device 43 informs the alarm inhibitor 36 to instruct the alarm controller 32 to cancel the alarm inhibit condition.

If desired, each transmitter can be uniquely coded, so as to provide a record of all individuals that render assistance to the individual being monitored. The receiver detects the unique code transmitted by the transmitter, and logs predetermined data, such as, for example, the transmitter id code, data and time that the signal was received. When the transmitter signal is lost, another record is made denoting the transmitter id code, date and time that the signal was lost. Thus, a record of all persons rendering assistance to the monitored individual would be available to the hospital personnel.

Figure 6:
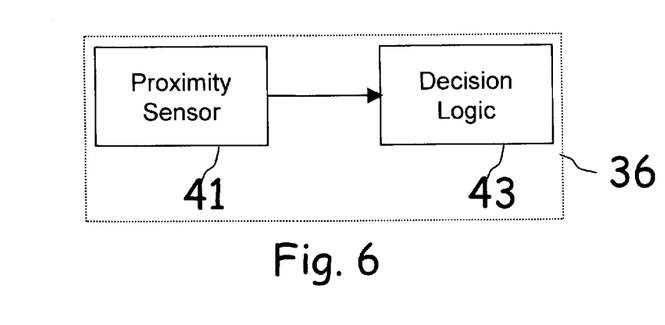
FIG. 6 illustrates a fourth embodiment of the alarm inhibitor.

In a variation of this embodiment, the transmitter is replaced with a security tag (transponder), similar to the security tags applied to consumer goods sold at apparel and department stores. These tags generally contain a passive (e.g., non-electrically powered), tuned circuit that is triggered and powered by an external electromagnetic field of a proximity sensor 41 (see FIG. 6). Subsequently, it responds with an RF signal transmission which inhibits the alarm. In this variation, the field generator would be located in the proximity of the bed or other supportive structure. When the caretaker, carrying the security tag (transponder), comes within range of the bed, the security tag is activated by the generated field of the proximity sensor 41. The transmitted response is detected, and used to issue the alarm inhibit signal.

In still another embodiment, the caretaker does not need to wear (or carry) a transmitter, and does not need to actuate a switch to temporarily deactivate the alarm. In this embodiment, the image processor 28 is utilized to determine when the alarm should be deactivated (see FIG. 7). When a caretaker enters the detecting zone 15 of the monitored individual's room, the monitoring system 10 senses the presence of a "new" (e.g., second) individual proximate the bed. When the second individual enters the bed monitoring zone, the image processor 28 analyzes the signals provided by the optical system 20 and concludes that the object is moving from "outside" the bed to "inside" the bed. Thus, the image processor 28 concludes that a second individual (e.g., a caretaker or other individual) that is rendering assistance to the monitored individual is present, and instructs the decision logic device 43 of the alarm inhibitor 36 to issue an alarm inhibit signal.

Figure 7:
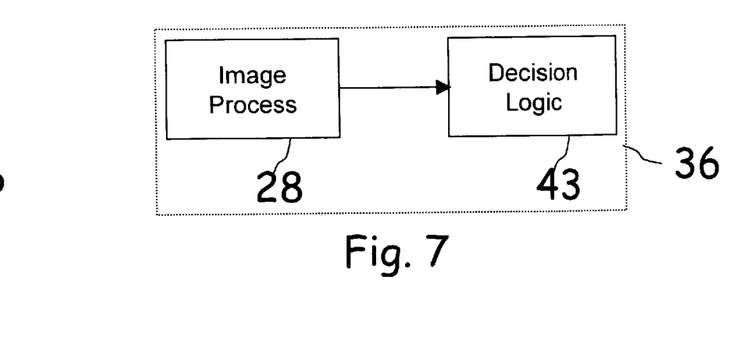
FIG. 7 illustrates a fifth embodiment of the alarm inhibitor.

The monitoring device continues to inhibit the alarm until such time that a determination is made that the caretaker is no longer assisting the patient. In particular, when the image processor determines that the caretaker's movements have been from "inside" the bed to "outside" the bed, the alarm inhibit signal is canceled to re-activate the monitoring system.

When the caretaker leaves the detecting zone 15, for any period of time, no matter how short, to, for example, obtain a glass of water for the patient, the alarm inhibit signal will be canceled. Thus, continuous monitoring will be provided whenever the caretaker is absent. When the caretaker returns and approaches (e.g., leans into) the bed again (e.g., moves from "outside" the bed to "inside" the bed), the alarm inhibit signal will be re-issued.

While preferred embodiments of the invention have been shown and described, various alterations and changes may be made without departing from the spirit and/or scope of the invention. For example, the present invention can be modified to include voice communication between the individual being monitored and the monitoring personnel. In this way, the monitoring personnel can communicate with the individual, and, for example, attempt to dissuade the person from actually exiting the bed, when the monitoring system determines that the person being monitored is attempting to exit the bed.

In addition, the alarm inhibitor can comprise a voice recognition device that recognizes a voice "signature" of one or more caretakers. In this way, the caretaker can inhibit the alarm by, for example, speaking a predetermined phrase. The alarm may be inhibited, for example, until it is manually re-set or until a predetermined time period elapses. If the alarm is inhibited for a predetermined period of time, the time period may optionally be extended (reset) by repeating the predetermined phrase. Alternatively, different phrases may be employed for different time periods during which the alarm is inhibited.

A further alteration and/or change that may be made to the present invention includes the "blanking" (tuning OFF) of the video image provided to the monitor while the alarm is disabled. In this way, the monitored individual's privacy is protected during certain procedures, such as, for example, when the caretaker undresses the individual. If desired, the image of the monitored individual on the monitor may be replaced by a message (and/or symbol) conveying that the image is intentionally blanked.

In addition, the present invention can be interfaced to a mobile alert device, such as, for example, a pager system, telephone system, computer system, portable palm top computer, wearing device (with or without a visual display), etc., via a monitoring station communicator 37 (see FIG. 2) to be used as an extension of the control station. The monitoring station communicator 37 accepts the signals that are provided to the monitoring station (e.g., visual signals provided to monitor 34 and audible signals provided to indicator 35), and forwards them to the above-mentioned mobile alert device(s). Such an arrangement allows the monitoring personnel to be mobile. For example, the monitoring personnel could be walking the halls of the nursing home performing tasks, such as, for example, attending to their assigned "patients". If a person attempts to exit their bed, the monitoring system can automatically activate the monitoring person's pager, informing that person as to which monitored person is attempting to exit their bed. Alternatively, each monitoring person could carry a portable computer (interfaced to the system via, for example, a wireless link) while they perform their regular tasks. When an alarm is actuated, the monitoring person can examine the display on their computer to determine which individual requires immediate attention.

While the above variation provides for the automatic alert of the pager, computer, wearing device, etc., a modification provides for a person to be located at the remote location and to manually activate the pager, computer, wearing device, etc. of the monitoring personnel.

It is also noted that these mobile devices can be configured to provide the same functionality as the equipment at the remote location.

The present invention has been described with respect to a single monitoring device and remote location. However, it is understood that in practice, a large number of monitoring devices will be utilized at a facility. Further, the present invention can be adapted to have a plurality of remote monitoring stations, which may be stationary and/or mobile.

Also, while the present invention has been described with respect to the monitoring of an individual lying in a bed in a nursing home, the present invention can be used to monitor any person that is susceptible to falling, either due to, for example, physical or mental illness, in any environment.

I claim:

1. An apparatus that determines when a monitored individual is likely to exit a supportive structure, comprising:
   an image capturing device that captures successive images of the monitored individual in the supportive structure;

a processing device that processes said captured images to detect predetermined characteristics of the monitored individual with respect to the supportive structure, by comparing a current captured image to a previous image, said predetermined characteristics comprising at least one of a relative position, a velocity, and an acceleration of the monitored individual relative to the supportive structure; and an alarm that is actuated when said processing device determines that said detected predetermined characteristics exceed predetermined threshold values for at least one of said predetermined characteristics.

2. The apparatus of claim 1, wherein said image capturing device detects at least one of visible light and infrared light emitted by the monitored individual and the supportive structure.

3. The apparatus of claim 1, wherein said image capturing device detects electromagnetic energy of a predetermined wavelength range emitted by the monitored individual and the supportive structure.

4. The apparatus of claim 1, further comprising an image signature database that stores each image captured by said image capturing device, a plurality of stored images being provided to said processing device, for analysis along with said captured image, to detect said predetermined characteristics.

5. The apparatus of claim 1, wherein said alarm is provided to a monitoring site remote from the monitored individual.

6. The apparatus of claim 1, further comprising an alarm inhibitor that enables a caretaker to render assistance to the monitored individual without actuating said alarm.

7. The apparatus of claim 6, wherein said alarm inhibitor is enabled by an actuation of a switch.

8. The apparatus of claim 7, wherein said actuation of said switch actuates a timer that prevents said alarm from being actuated for a predetermined period of time.

9. The apparatus of claim 6, wherein said alarm inhibitor comprises a transmitter that is in the possession of the caretaker, and a receiver that receives a signal transmitted by said transmitter.

10. The apparatus of claim 9, wherein said alarm is prevented from being actuated as long as said receiver receives said signal transmitted by said transmitter.

11. The apparatus of claim 1, wherein said alarm is prevented from being actuated as long as said image processor detects a second moving object proximate the monitored individual that is moving towards a center of said supportive structure.

12. The apparatus of claim 1, wherein said processing device utilizes an image recognition algorithm to determine at least one of position information and movement information of the monitored individual.

13. The apparatus of claim 1, further comprising a mobile alert device that is utilized by an individual distant from the monitored individual to be informed that the monitored individual is likely to exit the supportive structure.

14. The apparatus of claim 1, wherein said processing device is located at a location remote from the monitored individual.

15. The apparatus of claim 1, further comprising a visual device that provides a visual display of the monitored individual.

16. The apparatus of claim 15, further comprising a sequencing device that sequentially displays images of a plurality of monitored individuals on said visual device.

17. The apparatus of claim 15, further comprising a screen splitting device that enables images of a plurality of monitored individuals to be simultaneously displayed on said visual device.

18. The apparatus of claim 15, further comprising an information inserting device that superimposes information, associated with the monitored individual, on said visual display.

19. The apparatus of claim 1, further comprising a compressing device that compresses said captured image.

20. The apparatus of claim 19, wherein said captured image is digitally compressed.

21. The apparatus of claim 1, further comprising a communicating device that enables a person alerted to a possible exit situation by said alarm to communicate with said monitored individual.

22. An apparatus that determines when a monitored individual is likely to exit a supportive structure, comprising:

means for capturing successive images of the monitored individual in the supportive structure;

means for processing said captured images to detect predetermined characteristics of the monitored individual with respect to the supportive structure, by comparing a current captured image to a previous captured image, said predetermined characteristics comprising at least one of a relative position, a velocity, and an acceleration of the monitored individual relative to the supportive structure; and means for indicating that the monitored individual is likely to exit the supportive structure when said processing means determines that said detected predetermined characteristics exceed predetermined threshold values for at least one of said predetermined characteristics.

23. The apparatus of claim 22, wherein said capturing means comprises a sensor that detects at least one of visible light and infrared light emitted by the monitored individual and the supportive structure.

24. The apparatus of claim 22, wherein said capturing means comprises a sensor that detects electromagnetic energy of a predetermined wavelength range emitted by the monitored individual and the supportive structure.

25. The apparatus of claim 22, further comprising means for inhibiting said indicating means when a caretaker renders assistance to the monitored individual.

26. The apparatus of claim 25, wherein said inhibiting means comprises a switch.

27. The apparatus of claim 26, further comprising a delay device that prevents said indicating means from indicating that the monitored individual is likely to exit the supportive structure for a predetermined period of time upon an actuation of said switch.

28. The apparatus of claim 25, wherein said inhibiting means comprises a transmitter that is in the possession of the caretaker, and a receiver that receives a signal transmitted by said transmitter.

29. The apparatus of claim 28, wherein said indicating means is prevented from indicating that the monitored individual is likely to exit the supportive structure as long as said receiver receives said signal transmitted by said transmitter.

30. The apparatus of claim 25, wherein said inhibiting means comprises a voice recognizing device.

31. The apparatus of claim 22, wherein said indicating means is prevented from indicating that the monitored individual is likely to exit the supportive structure as long as said processing means detects that a second moving object proximate the monitored individual is moving towards a center of said supportive structure.

32. The apparatus of claim 22, wherein said indicating means comprises at least one of an audible alarm and a visual alarm.

33. The apparatus of claim 22, further comprising means for remotely alerting an individual distant from the monitored individual that the monitored individual is likely to exit the supportive structure.

34. A method for determining when a monitored individual is likely to exit a supportive structure, comprising:

capturing successive images of the monitored individual in the supportive structure;

processing the captured images to detect predetermined characteristics of the monitored individual with respect to the supportive structure, by comparing a current captured image to a previous image; and indicating that the monitored individual is likely to exit the supportive structure when it is determined that at least one predetermined characteristic exceeds a predetermined threshold value, wherein the processing of captured images analyzes the captured images to determine at least one of a relative position, a velocity, and an acceleration of the monitored individual relative to the supportive structure.

35. The method of claim 34, wherein the capturing of successive images comprises using an image capturing device.

36. The method of claim 34, wherein the indicating that the monitored individual is likely to exit the supportive structure comprises alerting an individual remote from the monitored individual.

37. An apparatus that determines when a monitored individual is likely to exit a supportive structure, comprising:

an image capturing device that captures successive images of the monitored individual in the supportive structure;

an image processing device that processes said captured images to detect at least one of a relative position, a velocity and an acceleration of the monitored individual with respect to the supportive structure, by comparing a current captured image to a previous image;

a motion threshold setting device that sets a predetermined characteristic for at least one of said relative position, said velocity and said acceleration of the monitored individual with respect to the supportive structure;

an alarm that is actuated when said at least one of said relative position, said velocity and said acceleration, detected by said image processing device, exceeds said predetermined characteristic; and an alarm inhibitor that inhibits said alarm when a caretaker renders assistance to the monitored individual.

38. The apparatus of claim 37, wherein said alarm is actuated at a monitoring station.

39. The apparatus of claim 38, further comprising a monitoring station communicator that transmits at least one of image, status and control signals to a mobile alert device.

40. The apparatus of claim 38, further comprising a display unit, located at said monitoring station, that provides a visual indication of the monitored individual.

41. The apparatus of claim 40, further comprising a sequencing device that sequentially displays images of a plurality of monitored individuals on said display unit.

42. The apparatus of claim 40, further comprising a screen splitting device that enables images of a plurality of monitored individuals to be simultaneously displayed on said display unit.

43. The apparatus of claim 37, wherein said image capturing device detects visible light.

44. The apparatus of claim 37, wherein said image capturing device detects visible light and infrared light.

45. The apparatus of claim 37, further comprising an image signature database that stores each image captured by said image capturing device, a plurality of stored images being provided to said image processing device, along with a current captured image, to detect said at least one of said relative position, said velocity and said acceleration.

46. The apparatus of claim 37, wherein said alarm inhibitor comprises a switch.

47. The apparatus of claim 46, wherein said switch actuates a timer that prevents said alarm from being actuated for a predetermined period of time.

48. The apparatus of claim 46, wherein said switch comprises a pressure sensitive floor mat switch.

49. The apparatus of claim 46, wherein said switch comprises a sensor that detects floor deflection.

50. The apparatus of claim 37, wherein said alarm inhibitor comprises a transmitter associated with a caretaker, and a receiver that receives a signal transmitted by said transmitter.

51. The apparatus of claim 50, wherein said alarm inhibitor inhibits said alarm as long as said receiver receives said signal transmitted by said transmitter.

52. The apparatus of claim 37, wherein said alarm inhibitor inhibits said alarm as long as said image processing device detects a second moving object, proximate the monitored individual, moving towards a center of said supportive structure.

53. The apparatus of claim 37, wherein said alarm inhibitor comprises a voice recognizing device.

54. The apparatus of claim 37, further comprising an information inserting device that provides predetermined data related to the monitored individual.

55. The apparatus of claim 54, wherein said predetermined data comprises at least one of a name of the monitored individual and a location of the monitored individual.

56. The apparatus of claim 37, further comprising a compressing device that compresses said images captured by said image capturing device.

57. The apparatus of claim 56, wherein said captured images are digitally compressed.

58. The apparatus of claim 37, further comprising a communicating device that enables a person alerted to a possible exit situation, by said alarm, to communicate with said monitored individual.

* * * * *